US00PP37715P3

(12) United States Plant Patent
Eremin et al.

(10) Patent No.: US PP37,715 P3
(45) Date of Patent: Sep. 29, 2026

(54) ***PRUNUS* ROOTSTOCK NAMED 'RVL-4'**

(50) Latin Name: ***Prunus cerasus* x *maackii* x *lannesiana***
Varietal Denomination: RVL-4

(71) Applicants: Gennady Eremin, Krymsk (RU); Oxana Eremin, Krymsk (RU)

(72) Inventors: Gennady Eremin, Krymsk (RU); Oxana Eremin, Krymsk (RU)

( * ) Notice: Subject to any disclaimer, the term of this patent is extended or adjusted under 35 U.S.C. 154(b) by 0 days.

(21) Appl. No.: 19/301,524

(22) Filed: Aug. 15, 2025

(65) Prior Publication Data

US 2026/0060155 P1 Feb. 26, 2026

Related U.S. Application Data

(60) Provisional application No. 63/686,300, filed on Aug. 23, 2024.

(51) Int. Cl.

| | |
|---|---|
| ***A01H 5/06*** | (2018.01) |
| ***A01H 5/12*** | (2018.01) |
| ***A01H 6/74*** | (2018.01) |

(52) U.S. Cl.
USPC ..... Plt./183
CPC ..... *A01H 6/7445* (2018.05); *A01H 5/06* (2013.01); *A01H 5/12* (2013.01)

(58) Field of Classification Search
USPC ..... Plt./180, 181, 183
See application file for complete search history.

(56) References Cited

U.S. PATENT DOCUMENTS

PP27,952 P3 * 5/2017 Lewis ..... A01H 6/7427 Plt./155

OTHER PUBLICATIONS https://plants.usda.gov/ for species search in plant database (Year: 2025).*

* cited by examiner

*Primary Examiner* — Susan Mccormick Ewoldt
*Assistant Examiner* — Zachariah Allan Kay

(57) ABSTRACT

A new and distinct cultivar of *Prunus* rootstock tree named 'RVL-4' is disclosed, characterized by high precocity and mildew resistance. 'RVL-4' is suitable for use as a rootstock upon which commercial fruit bearing sweet cherry varieties may be budded or grafted. The new variety is a *Prunus cerasus* x *maackii* x *lannesiana*, produced for rootstock.

3 Drawing Sheets

Latin name of the genus and species: *Prunus cerasus* x *maackii* x *lannesiana.*

Variety denomination: 'RVL-4'.

BACKGROUND OF THE INVENTION

The new cultivar is a product of a planned breeding program. The new variety resulted from a cross pollination breeding program conducted in Krymsk, Russia The seed parent is the unpatented variety *Prunus cerasus* x *maackii* 'Rubin'. The pollen parent is the unpatented variety *Prunus lannesiana* 'L2' The cross pollination resulting in the new cultivar occurred during 1995. The new variety was first selected in 2004, by the inventors in Krymsk, Russia.

Asexual reproduction of the new cultivar 'RVL-4' by vegetative cuttings was first in performed in 2004 at a nursery in Krymsk, Russia and after 15 years of confidential testing has shown that the unique features of this cultivar are stable and reproduced true to type on successive generations.

FIELD OF THE INVENTION

The new cultivar 'RVL-4' *Prunus cerasus* x *maackii* x *lannesiana* has been developed and selected as a rootstock for trees used for commercial cherry fruit production.

SUMMARY OF THE INVENTION

The cultivar 'RVL-4' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'RVL-4'. These characteristics in combination distinguish 'RVL-4' as a new and distinct *Prunus* cultivar:

1. Suitability for use as a rootstock upon which commercial fruit bearing sweet cherry varieties may be budded or grafted.
2. High precocity.
3. Mildew resistance.
4. Induces healthy lateral branch development.

DESCRIPTION OF THE RELATED ART

Parental Comparison

Plants of the new cultivar 'RVL-4' differs from plants of the seed parent in the following:

1. The seed parent is a semi-dwarf tree growing to about 70% of the size of the new cultivar.

Plants of the new cultivar 'RVL-4' differs from plants of the pollen parent in the following:

1. The pollen parent is more vigorous, growing to about 120% of the size of the new cultivar.
2. The pollen parent exhibits reduced rootstock performance (poor growth of the grafted variety) in both drought and very wet soil conditions.

Commercial Comparison

Plants of the new cultivar 'RVL-4' are similar to plants of the known commercial variety 'L5', unpatented in most horticultural characteristics, however, plants of the new cultivar 'RVL-4' differ in the following:

1. Increased precocity by one year.
2. Later flowering time by approximately 2 weeks.
3. Narrower foliage by about 30%.

BRIEF DESCRIPTION OF THE PHOTOGRAPHS

The accompanying photographs illustrate some typical characteristics of 'RVL-4'. The photographs were taken using conventional techniques and although colors may appear different from actual colors due to light reflectance it is as accurate as possible by conventional photographic techniques.

DETAILED BOTANICAL DESCRIPTION

Figure 1:
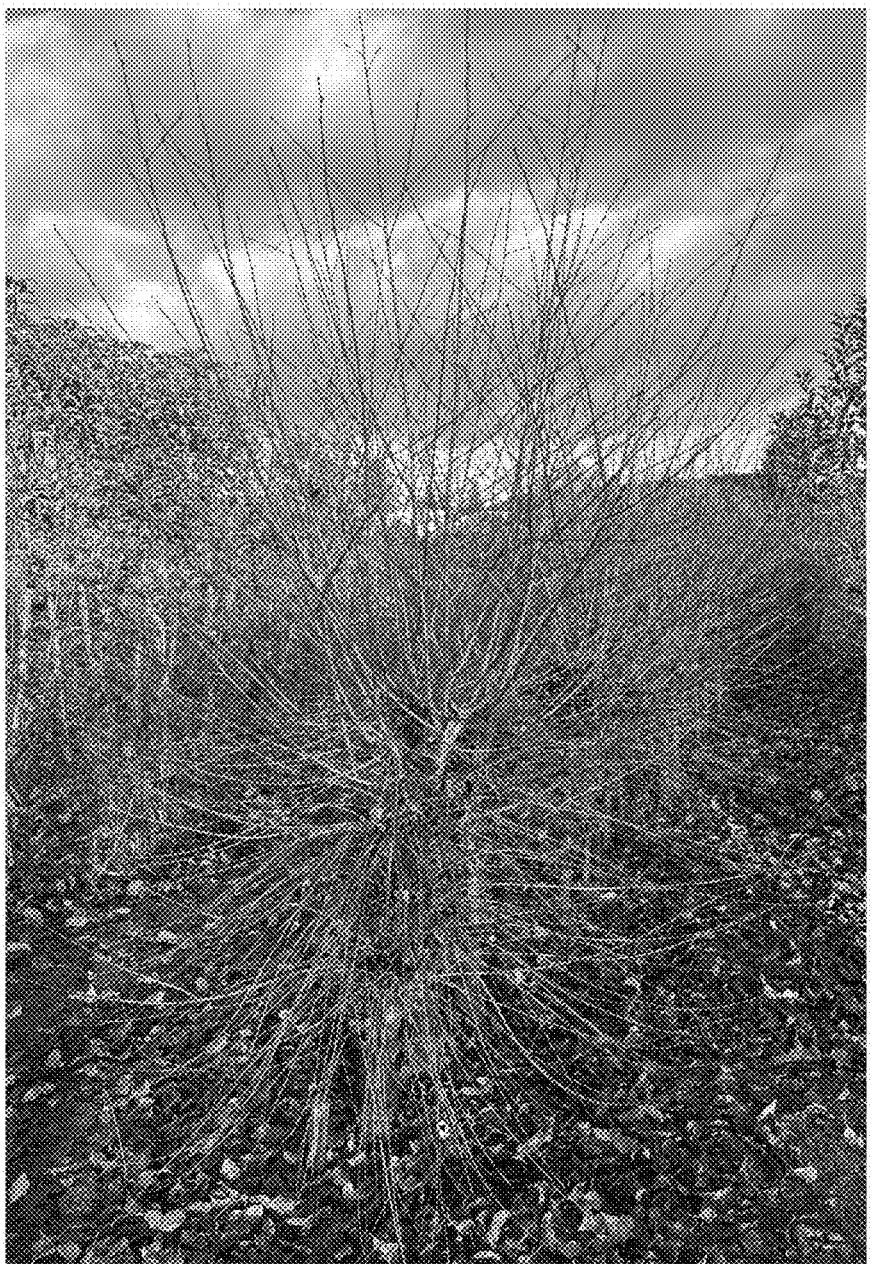
FIG. 1 shows an approximately 3-year old tree of 'RVL-4' which has been cut back to generate new growth for propagation.
Figure 2:
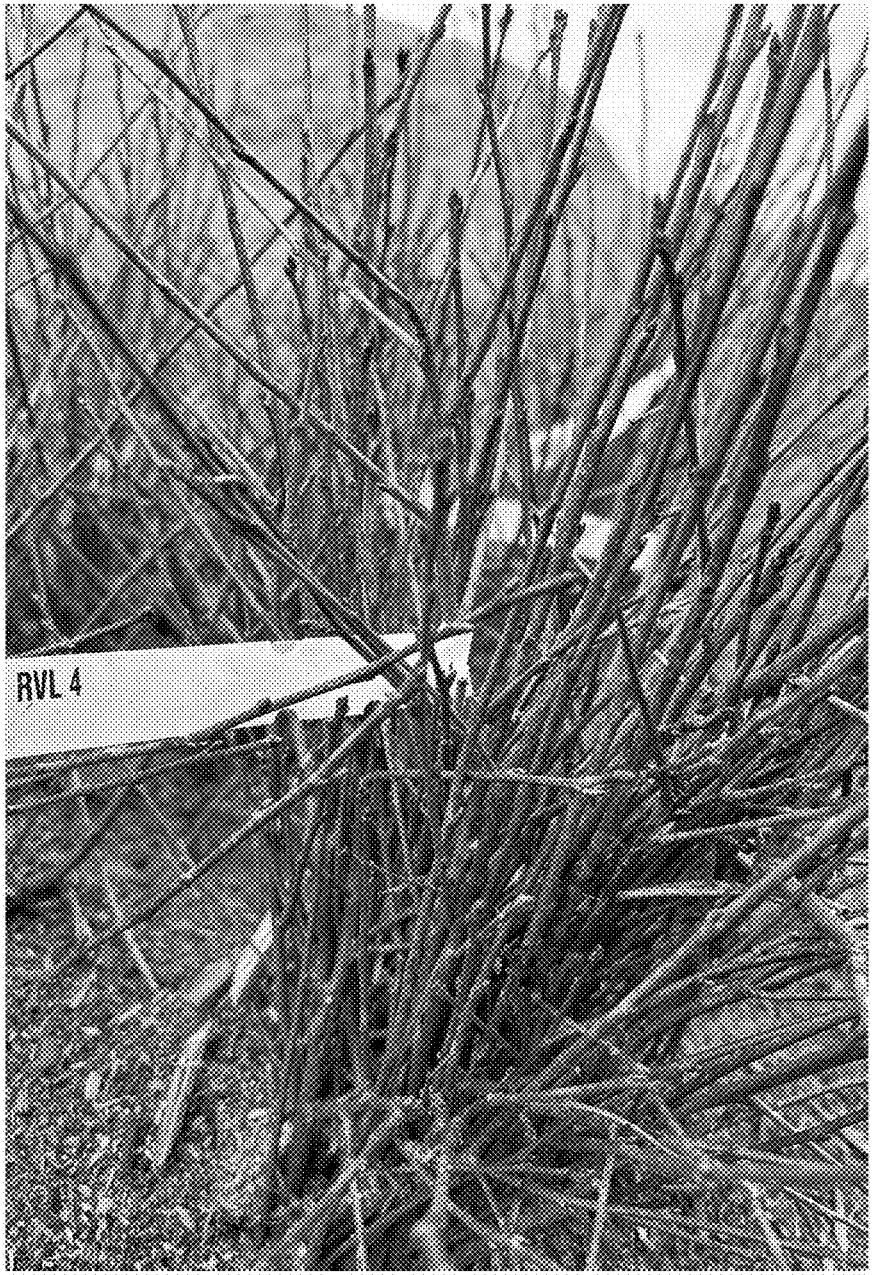
FIG. 2 is a close-up view of the new growth in FIG. 1.
Figure 3:
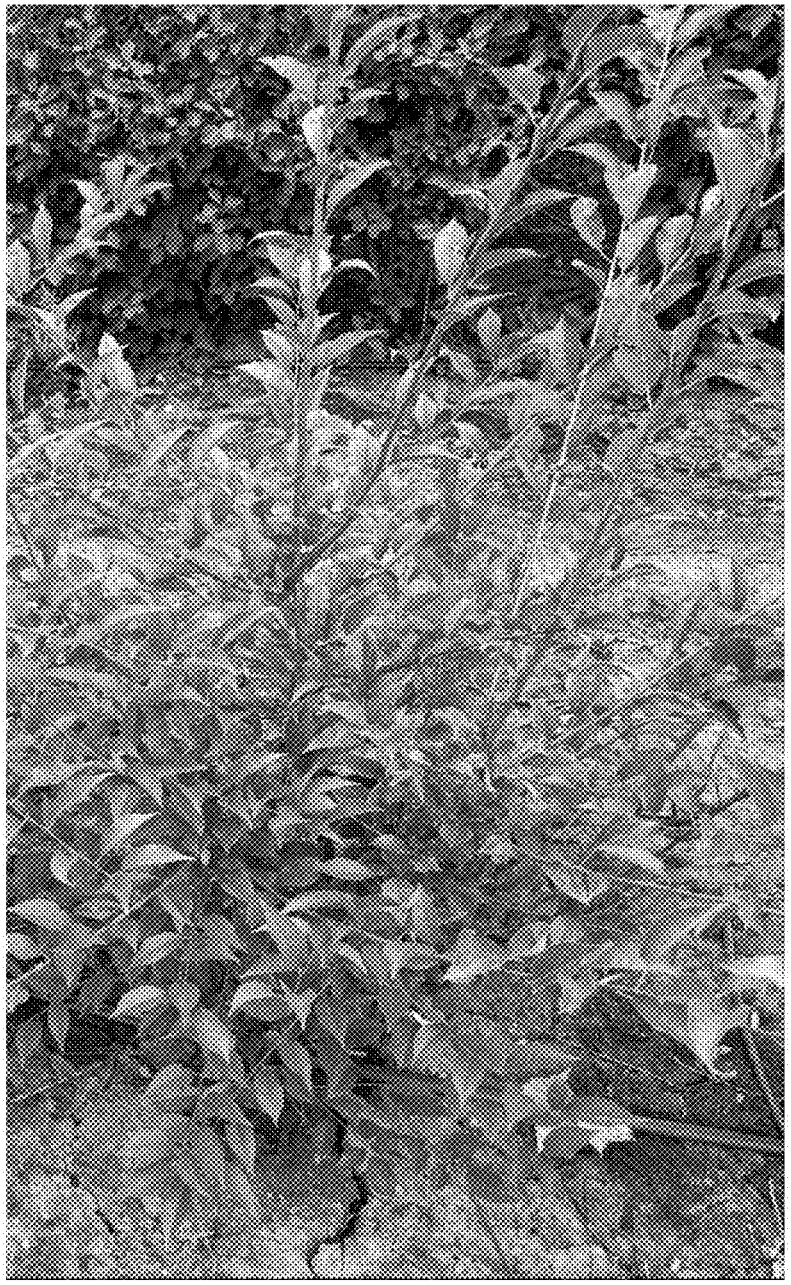
FIG. 3 shows a leafed out tree of 'RVL-4' at about 1.5 years of age.

In the following description, color references are made to The Royal Horticultural Society Colour Chart 2007 except where general terms of ordinary dictionary significance are used. The following observations and measurements describe 'RVL-4' plants grown outdoors in Krymsk, Russia. Measurements and numerical values represent averages of typical plant types.

Botanical classification: *Prunus* 'RVL-4'.

ROOTS

Root description: Typical *Prunus* root, coarse, semi-woody roots, typically colored near RHS Grey-Brown 199A.

TREE

Growth habit: Spreading deciduous tree.

Branching characteristics: Not typically grown for above ground characteristics.

One-year old shoot internode length: 4.2 cm.

*Texture*.—Lenticels present.

*Color*.—Striated near Grey-Brown 199A with Greyed-Orange N167A. Immature growth is colored near Greyed-Purple 187A with Greyed-Orange 177D dots.

Vegetative buds: Approximately 6 mm long and 4 mm wide. Colored near Yellow-Green N144C, heavily flushed Greyed-Purple 187A.

Wood color: Greyed-Orange 165A.

Trunk: No true trunk has been observed as frequent pruning cause only basal branching.

FOLIAGE

Leaf:

*Arrangement*.—Alternate.
*Shape*.—Narrow elliptic.
*Average length*.—8.5 cm.
*Average width*.—3.7 cm.
*Attachment*.—Stalked.
*Apex*.—Acute.
*Base*.—Blunt rounded.
*Margin*.—Serrate and crenate. Shallow.
*Texture of top surface*.—Glabrous, somewhat leathery.
*Texture of bottom surface*.—Glabrous.
*Pubescence*.—No leaf pubescence.
*Aspect*.—Flat to slightly undulating along margins.
*Color*.—Mature foliage upper side: Yellow-Green 147A. Mature foliage lower side: Yellow-Green 147B.
*Leaf petiole*.—Length: 1.5 cm. Diameter: 0.3 cm. Color: Near RHS Greyed-Orange 177A. Texture: Slightly pubescent.
*Stipule*.—Not present.
*Nectaries*.—2 round, green nectaries present at base of leaf blade.

FLOWER

Flower buds:

*Length*.—2.5 mm.
*Width*.—1.2 mm.
*Color*.—Near RHS Yellow-Green 145D.

Flowers:

*Number of flowers*.—About 5 flowers per 10 cm of new branch.
*Shape/form*.—Single whorl.
*Habit*.—Single flowers emerging along the length of lateral branches.
*Flowering season*.—Spring.
*Flower longevity*.—About 1 to 2 weeks.
*Fragrance*.—Weak intensity.
*Length*.—1.5 cm.
*Diameter*.—1.5 cm.
*Depth*.—0.75 cm.
*Angle*.—Outwards.
*Persistence*.—Self-Cleaning.

Petals:

*Number*.—5.
*Arrangement*.—Single whorl.
*Length*.—8 mm.
*Width*.—4 mm.
*Shape*.—*Elliptic*.
*Apex*.—Obtuse.
*Base*.—Cuneate.
*Margin*.—Entire.
*Texture*.—Both surface glabrous, soft, and silky.
*Color*.—Immature, upper surface: RHS White NN155A. Immature, lower surface: RHS White NN155A. Mature, upper surface: RHS White 155D. Mature, lower surface: RHS White 155D.

Sepals:

*Number*.—5.
*Arrangement*.—Whorl.
*General appearance*.—Inconspicuous.

*Length*.—2 mm.
*Width*.—1 mm.
*Shape*.—Narrowly elliptic.
*Apex*.—Obtuse.
*Base*.—Fused.
*Margin*.—Entire.
*Texture*.—Both surfaces very lightly pubescent.
*Color*.—Upper surface: RHS Greyed-Yellow 161B. Lower surface: RHS Greyed-Yellow 161B.

Calyx:
*Shape*.—Collar-like, sepals down-curled.
*Length*.—5 mm.
*Width*.—5 mm.

Peduncle:
*Length*.—1.5 cm.
*Width*.—1 mm.
*Color*.—RHS Greyed-Yellow 161B.
*Texture*.—Glabrous.
*Angle*.—About 45° relative to lateral branch.

REPRODUCTIVE ORGANS

Gynoecium:
*Pistil number*.—1.
*Pistil length*.—7 mm.
*Stigma shape*.—Globular.
*Stigma color*.—RHS Greyed-Yellow 161A.
*Style length*.—6 mm.
*Style color*.—RHS White 155A.
*Ovary color*.—RHS Green-White 157A.

Androecium:
*Stamen number*.—10 to 12.
*Filament length*.—5 mm.
*Filament color*.—RHS White 155A.
*Anther shape*.—Globular.
*Anther length*.—1 mm.
*Anther color*.—RHS Greyed-Yellow 161A.
*Pollen*.—Not observed.

OTHER CHARACTERISTICS

Fruits/seeds: Not observed.

Disease/pest resistance: Neither resistance nor susceptibility to pathogens and pests common to *Prunus* have been observed.

Temperature tolerance: The new variety is suitable for growing in USDA zones 5 through 9.

What is claimed is:

1. A new and distinct cultivar of *Prunus* tree named 'RVL-4' as herein illustrated and described.

* * * * *